US011850505B2

United States Patent
Chalmers et al.

(10) Patent No.: US 11,850,505 B2
(45) Date of Patent: Dec. 26, 2023

(54) FLAVOUR SYSTEM

(71) Applicants: Alan Chalmers, Kenilworth (GB); Ali Asadipour, Coventry (GB)

(72) Inventors: Alan Chalmers, Kenilworth (GB); Ali Asadipour, Coventry (GB)

(73) Assignees: Alan Chalmers, Kenilworth (GB); Ali Asadipour, Coventry (GB)

(*) Notice: Subject to any disclaimer, the term of this patent is extended or adjusted under 35 U.S.C. 154(b) by 0 days.

(21) Appl. No.: 17/974,837

(22) Filed: Oct. 27, 2022

(65) Prior Publication Data

US 2023/0051941 A1 Feb. 16, 2023

Related U.S. Application Data

(63) Continuation of application No. 17/011,427, filed on Sep. 3, 2020, now Pat. No. 11,517,814.

(51) Int. Cl.
| | |
|---|---|
| *A63F 13/28* | (2014.01) |
| *G06F 3/01* | (2006.01) |
| *A23L 27/20* | (2016.01) |
| *G09B 9/00* | (2006.01) |
| *G06F 16/25* | (2019.01) |
| *A63F 13/90* | (2014.01) |

(52) U.S. Cl.
CPC ............ *A63F 13/28* (2014.09); *A23L 27/20* (2016.08); *A63F 13/90* (2014.09); *G06F 3/011* (2013.01); *G06F 16/252* (2019.01); *G09B 9/00* (2013.01); *A23V 2002/00* (2013.01)

(58) Field of Classification Search
CPC ......... A63F 13/28; A63F 13/90; G06F 3/011; A63J 2005/008
See application file for complete search history.

(56) References Cited

U.S. PATENT DOCUMENTS

| | | | |
|---|---|---|---|
| 5,610,674 A | 3/1997 | Martin | |
| 6,231,032 B1 | 5/2001 | Ellwood et al. | |
| 2010/0077261 A1* | 3/2010 | Jung | G06Q 30/0603 |
| | | | 434/428 |
| 2013/0106690 A1 | 5/2013 | Lim | |

(Continued)

FOREIGN PATENT DOCUMENTS

| | | |
|---|---|---|
| CN | 107704088 | 2/2018 |
| CN | 110045835 | 7/2019 |

(Continued)

OTHER PUBLICATIONS

Iwata et al. "Food Simulator: A Haptic Interface for Biting", IEEE Virtual Reality, IEEE, Mar. 27-31, 2004, pp. 51-57.

*Primary Examiner* — Robert J Utama

(74) *Attorney, Agent, or Firm* — NIXON & VANDERHYE P.C.

(57) ABSTRACT

A system to deliver to a user artificial flavor sensations equivalent to a selected desired real flavor having a database in which is stored data of a number of real flavors broken down into components selected from taste, smell, feel and appearance, A head mounted display device is provided to deliver visual and audio cues of a flavor from the database and a bite sensation component is mounted in the mouth of a wearer of the head mounted display controlling the delivery of taste, feel, and smell components of the flavor to the user.

4 Claims, 4 Drawing Sheets

(56) References Cited

U.S. PATENT DOCUMENTS

| | | | |
|---|---|---|---|
| 2015/0366405 A1* | 12/2015 | Manchuliantsau | A23L 33/17 222/23 |
| 2017/0011164 A1 | 1/2017 | Adoni et al. | |
| 2018/0339847 A1 | 11/2018 | Neidle et al. | |
| 2019/0011700 A1 | 1/2019 | Reiner | |
| 2019/0041975 A1 | 2/2019 | Anderson | |
| 2022/0066539 A1 | 3/2022 | Chalmers et al. | |

FOREIGN PATENT DOCUMENTS

| | | | |
|---|---|---|---|
| WO | WO-2006127605 A2 * | 11/2006 | A23G 3/364 |
| WO | 2014/125289 | 8/2014 | |

* cited by examiner

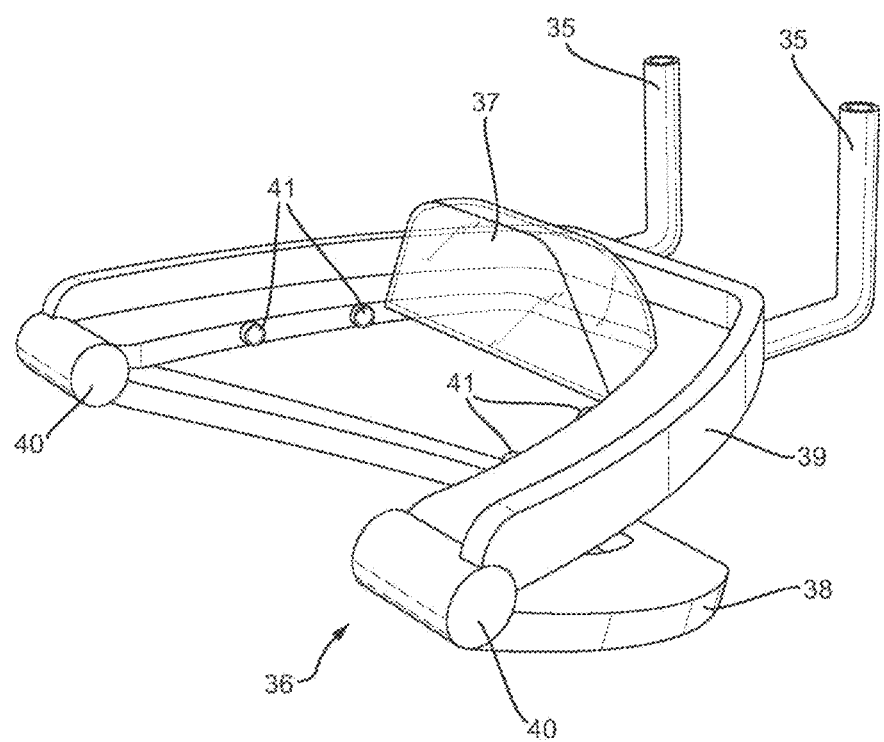

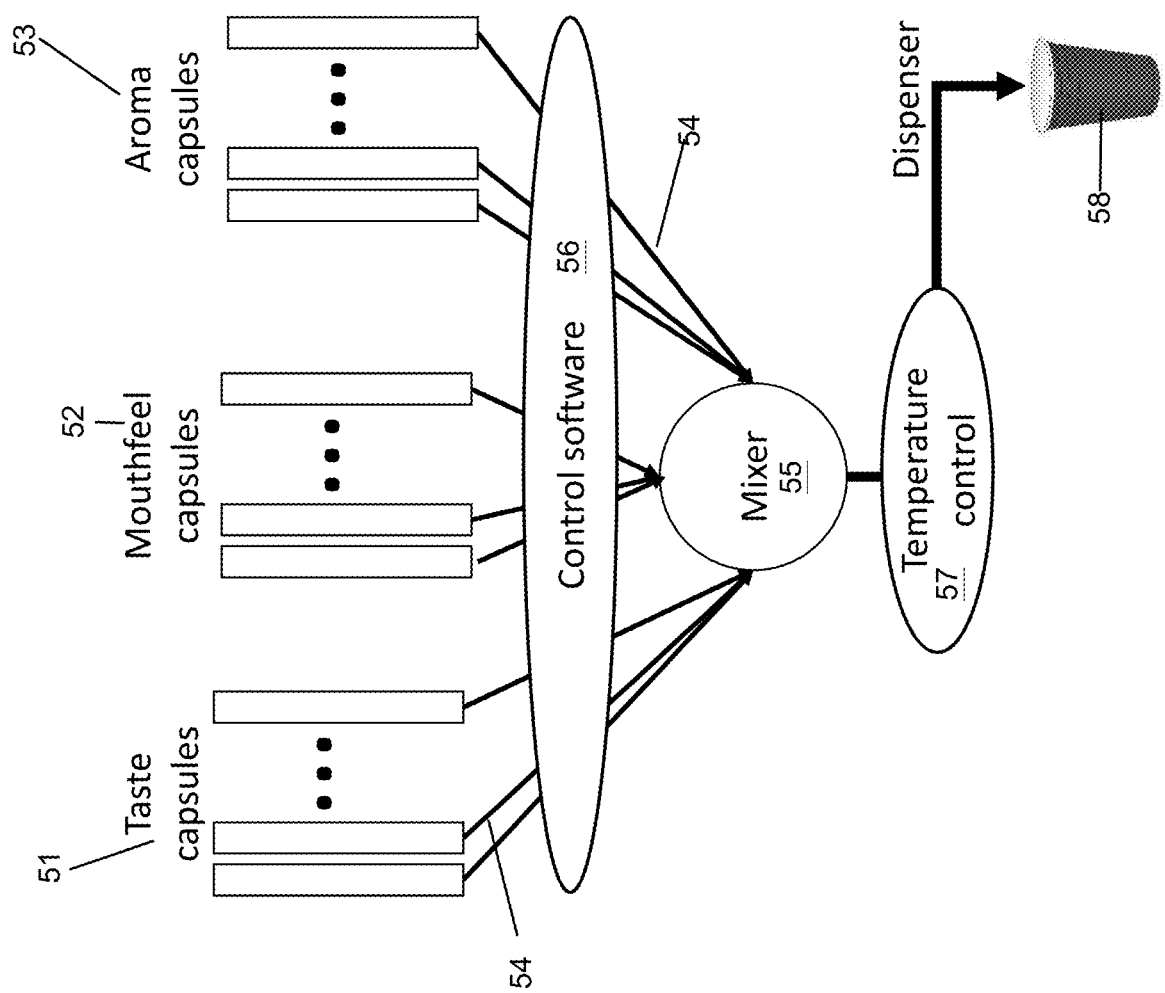

FLAVOUR SYSTEM

This application is a continuation of U.S. patent application Ser. No. 17/011,427 filed Sep. 3, 2020 (allowed), which is incorporated herein by reference.

FIELD OF THE INVENTION

This invention relates to the generation of flavor sensations.

BACKGROUND

Modern Virtual Reality technology has the ability, through immersive computer simulation, to deliver novel insights within a range of applications in a safe, controlled, and repeatable manner. In addition, the emerging field of flavor perception uses multisensory stimuli (visuals, audio, smell, feel, taste) as well as cognitive stimuli, especially descriptors e.g. "this is a rich and delicious flavor" and attention, e.g. "notice the subtle mint smell", to manipulate a person's perception of the flavor of a food or beverage Molecules of food are chemicals detected by taste receptors in the mouth, and the olfactory receptors in the nose. There are five primary tastes: salty, sour, bitter, sweet and umami (from the Japanese for "tasty"—which corresponds roughly to the taste of glutamate) [PS16]. How we perceive food is also influenced by its mouthfeel (eg. astringency, oiliness, capsaicin) texture, smell (both orthonasal ("sniffed in") and retronasal ("from the food in the mouth")), temperature, looks, cost, and environmental factors, such as where we are eating and with whom, etc. It has been shown previously that it is possible to simulate the sensation of some of the primary tastes by direct electrical and thermal stimulation of the tongue. Electrical stimulation has also been used to attempt the simulation of smell, with limited success so far. In addition, it is known that cross-sensory perception can influence enjoyment of food by superimposing virtual color onto a real drink, and it is also known that the perceived taste of a cookie can be changed using visual and auditory stimuli. How multisensory stimuli, in particular visuals, audio, smell and motion, may affect a real experience (singularly or in combination) has been studied extensively, including their impact on flavor perception, indeed, understanding the effect of the precision of multisensory stimuli simulation on virtual experiences. In addition, neuroscience work has shown that word level descriptors of taste, smell and flavor (e.g. "this food is rich in omega-3 fatty acids which have health benefits") have a top-down influence on the actual representations of the flavors in the secondary taste and olfactory cortices, which are in the orbitofrontal cortex. In contrast, top-down attention to the pleasantness of taste, smell, and flavor increases the response of the brain systems that represent their pleasantness (the orbitofrontal and anterior cingulate cortices). This implies that different brain systems are selectively upregulated when the instructions are to pay attention to intensity (including the quality of the stimulus, such as how sweet it is, or how sour) vs pleasantness or reward value. This neuroscience research suggests that our perception of flavor can indeed be manipulated with both sensory and cognitive stimuli. This invention goes further to create and deliver virtual flavors that are experience equivalent to real flavors.

SUMMARY OF INVENTION

According to the invention a system to deliver to a user artificial flavor sensations equivalent to a selected real flavor having
  a database in which is stored data of a number of real flavors broken down into the taste and smell components of the flavors;
  containers containing taste components namely: sweetness, sourness, saltiness, bitterness, umami, astringency, capsaicin;
  a delivery means controlled from the database to provide from the containers a flavor sensation corresponding to the selected real flavor.

The delivery means may deliver the taste components of the selected real flavor a cup or other vessel with any smell components.

In addition, appearance information may be stored in that database, the delivery means may additionally deliver the appearance of the selected real flavor.

The system will deliver virtual flavors that are "experience equivalent" to benchmark real flavors, in "experience equivalent" is meant one which achieves the very same cognitive response whether subjects are exposed to real or synthesized flavor stimuli.

The system may be combined with a virtual reality headset, which displays to a user images of surrounding in which the selected flavors may be experienced as sometimes, perceptions of flavors can be influenced by the surroundings in which they are experienced.

The system of the invention can be used as a diagnostic tool.

INTRODUCTION TO THE DRAWINGS

FIG. 3 illustrates a bite sensation component for use with the present invention; and FIG. 4 is a schematic diagram showing the combination of flavor sensations to a delivery vessel.

ILLUSTRATIVE EXAMPLES

Figure 1:
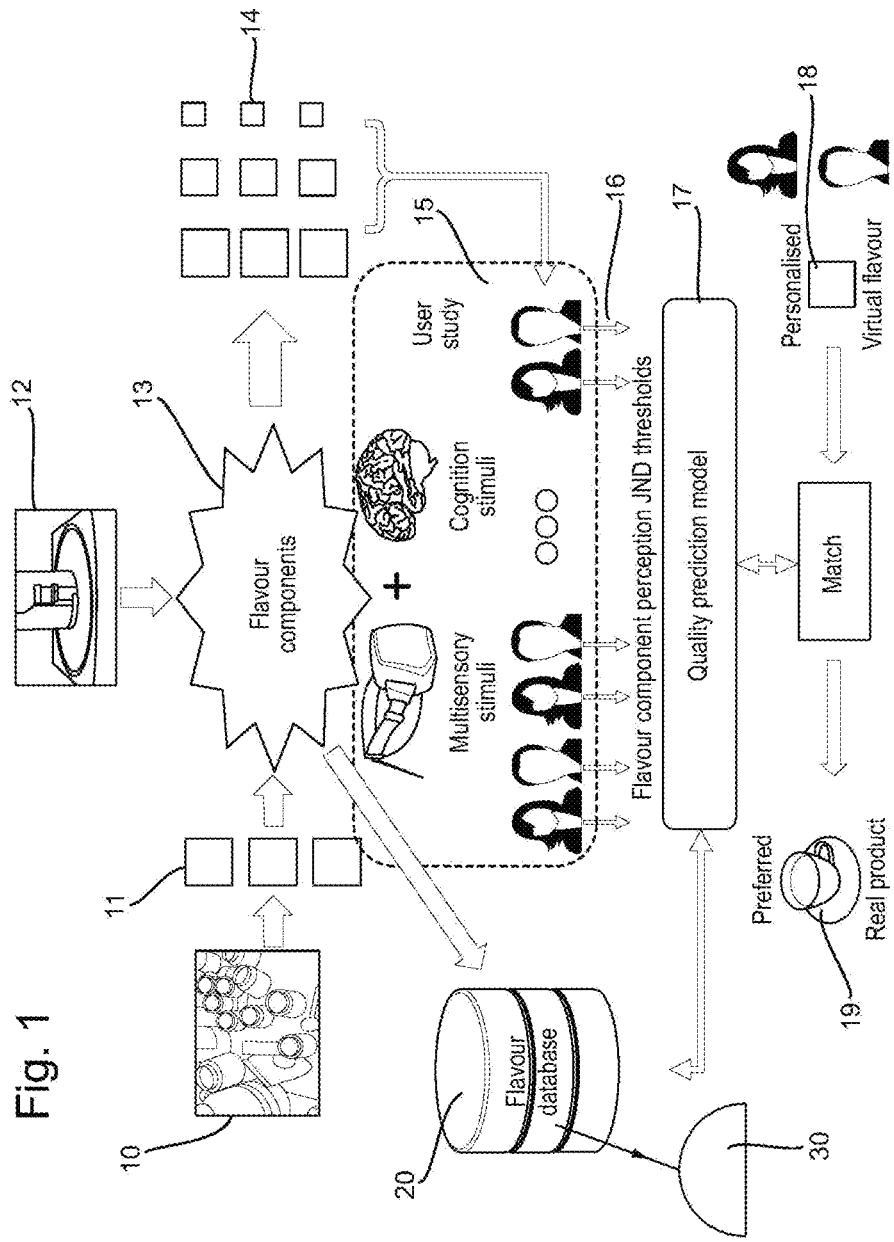
FIG. 1 illustrates the creation of a flavor database for use in the present invention.

FIG. 1 illustrates the creation of a flavors database 20 for use in the invention. The database 20 can deliver visual, audio, smell (both othornasal and retronasal), feel, and taste cues together with cognitive cues (visual and/or audio) through a head mounted device 30 of the invention (see description of FIG. 2 below). The virtual flavor system of the invention can predict, if the flavor components of a real sample are known, what the make-up of virtual sample components should be to achieve experience equivalence between the real and virtual sample. A benefit of this is that, if a personal choice of virtual flavor is specified, it should be possible to provide a blend of real product that matches this preference. The flavor components considered are multisensory stimuli (visual, audio, smell, feel, taste), cognitive stimuli (descriptors, attention), and the environment.

FIG. 1 shows how a flavor database for a target product is created. This is done by:
  a. Firstly, creating samples 11 of the target product 10 (in this example a tea was used) including any blends; or by analyzing a new food or drink product 12;

b. Secondly 13, analyzing these samples to extract their flavor components; these are fed to the database 20 and to generate virtual samples 14, comprising:
   i. visual information—the color profile;
   ii. audio information—any related sounds such as crunch (these are recorded from a microphone in the mouth);
   iii. smell—using Gas Chromatography Mass Spectrometry analysis;
   iv. taste—by means of an Insent™ TS-5000Z (made by Intelligent Sensing Technology, Inc of Japan) which can provide taste quality and intensity information; the same as would be perceived by a human;
   v. feel (namely mouthfeel, temperature, and "hardness")—by means of an Insent™ TS-5000Z (made by Intelligent Sensing Technology, Inc of Japan) which can provide mouthfeel quality and intensity information; the same as would be perceived by a human, the normal temperature at which the product is consumed, and how firm it is (this latter would not be required for a liquid).
c. Thirdly, associating cognitive cues with each sample. These comes from focus groups 15, and prior knowledge such as "flavor wheels", etc.
   i. Descriptors—e.g. this food is healthy for you;
   ii. Attention—e.g. pay attention to the hint of vanilla.
d. Precision setting: Once the flavor database has been established, the Just Noticeable Difference (JND) thresholds 16 between flavor components of real 11, 12, and virtual samples 14 need to be determined. This is currently achieved via a user study using a two-interval forced choice (2IFC) method. In addition, questionnaire techniques evaluate in detail the perceived realism, technical performance and user acceptance of a virtual flavor and a suite of standard sensory organ tests are used from existing well validated tests for sight, hearing, and sense of taste and smell. Two Quality Prediction Models (QPM1 and QPM2) 17 are established from all the experimental data to specify the minimum precision of the virtual multisensory and cognitive stimuli that are required in order that a virtual sample is perceived as being equivalent to a real sample. These QPMs consider five senses as well as the cognitive stimuli. QPM1 takes as input the real sample flavor components from the database 20 independent of the given scenario, while QPM2 has the additional dimension of including how the environment may affect this precision, and thus the Quality Prediction Models thus take into account both the components and the scenarios. Finally, the accuracy of the QPMs is validated against previously unused real samples and an untested scenario (QPM2).

Figure 2:
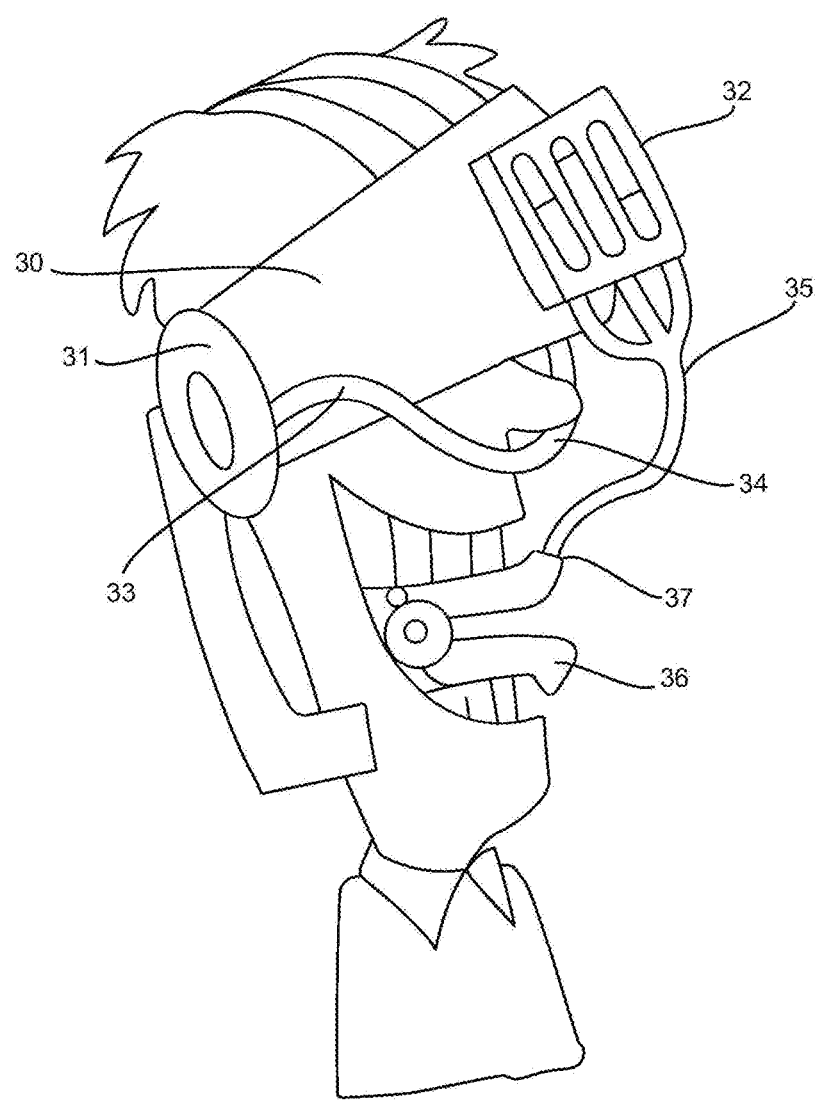
FIG. 2 illustrates a modified head mounted device used in the present invention.

The outcome of the Quality Prediction Models is then compared with a user's preferred virtual flavor 18 derived as discussed in relation to FIGS. 2 and 3. If there is a match that generates parameters of a preferred item 19 (a tea blend in the illustrated example) to be marketed or used.

FIG. 2 shows the modified head mounted device 20 used in connection with the virtual flavor system of the present invention. In the trial system developed by the applicant, the head mounted device is a modified head mounted display device 30, but a special purpose device could be used instead. Visual and audio cues are delivered from the database 20 through the head mounted device's existing visual and audio inputs 31.

In addition to the visual and audio flavor components, cognitive stimuli are also delivered through these interfaces.

Taste, mouthfeel, and smell are provided from tanks 32 and delivered through tubes 35 to the tongue through a reservoir 37 (see FIG. 3) associated with bite sensation component 36. The basic taste is provided from six tanks 32 containing liquids to provide the basic tastes, namely the sweet, sour, salty, bitter (×2) and umami stimuli, and three additional tanks to provide astringency, oiliness, and a "chilli sensation" (capsaicin). Two different solutions are provided for the bitter taste, as the human tongue is particularly sensitive to bitterness. This is "evolutionary" and is related to the fact that bitter substances often could be poisonous.

Table 1 shows example chemical solutions used in this example to deliver each of the taste and mouthfeel stimuli.

TABLE 1

| Taste | Virtual solution |
| --- | --- |
| Sweet | Sucrose |
| Sour | Tartaric Acid |
| Salty | Potassium Chloride |
| Bitter (×2) | Quinine Hydrochloride |
|  | Iso-alpha acid |
| Umami | Monosodium glutamate |
| Astringency | Tannic Acid |
| Oiliness | Rape seed oil |
| Capsaicin | Chilli Solution |

Smell has a major effect on how humans experience flavor. Humans' smell brain is an integral part of mood, feeling and long-term memory centers and most smells are coded based on a hedonic response. A smell can be complex, for example the smell of coffee can contain 10,000 different smell molecules. However, the human nose, unless it is specifically trained, is unable to identify more than a few of the most dominant smell molecules in a complex smell, which simplifies the task underlying this invention. This reduction in smell sensation is especially true if the person is experiencing other sensory stimuli (e.g. visual, audio, taste, feel) at the same time and is thus not focusing only on the smell component.

It is possible to achieve equivalent smells with a subset of the real smells and other cues. The flavor delivery system contains smell capsules with the tubes 32 and further smell capsules in delivery tubes, to deliver smell to the nose 34 through a cannula 33. The number of capsules used is related to how many key smells are associated with target product and its blends. To deliver smell, taste and mouthfeel, a small amount of the appropriate percentage of each taste and mouthfeel components (known from the flavor database) is pumped into the reservoir 37 (FIG. 3), here it is mixed with the appropriate smell components (also known from the flavor database) and heated/cooled to the appropriate temperature. The mixture is then squirted softly through atomizers (41 in FIG. 3) into a container, such as a cup, or into the user's mouth across the top of his/her tongue. The direction and intensity of this squirt into the mouth is based on the position of the taste buds and saliva glands that should be stimulated (known from the flavor database). At the same time, if a cup is not being used, additional smell molecules are released in front of the user's nose 34 from a tube 33. It is necessary to include both smell delivery systems to ensure both orthonasal ("sniffed in") and retronasal ("from the food in the mouth") smells. If a cup is used, the user will acquire the orthonasal smell as the virtual flavor is consumed.

Bite sensation is used to simulate the firmness of the target food. The bite sensation component 36 is illustrated in greater detail in FIG. 3. The bite sensation component comprises a lower jaw 38, and an upper jaw 39, in which the atomizers 41 are mounted and which are coupled to the reservoir by tubes (not shown). The lower and upper jaws are pivotally mounted with respect to one another by a pair of force adjustable hinges 40, which are biased to the open position shown, by spring means. As the user bites down on the bite sensation component 36, sensations are released from the reservoir 37 thought the atomizers 41 into his/her mouth through the atomizers 41. In addition to releasing the taste, the resistance provided by the bite sensation component 36, by virtue of the force adjustable hinge 40 delivers the bite texture. The harder the food, the more resistance from adjustable hinge 40. This required level of resistance for the bite sensation component is set from the flavor database.

The reservoir 37, as shown is in the mouth, however, it could be mounted so that it is outside the mouth. The position of the atomizers 41, can also be varied in different designs, to suit the position of parts of the mouth most sensitive to a taste and smell components of a product.

To derive the user's personalized virtual flavors, different combinations of taste, appearance, smell, feel, sound can be controlled by the user and directed to him/her through the bite sensation component. Alternatively the personalized virtual flavors can be controlled by software algorithms, The user's flavor, preferences as determined by his/her choice of the various combinations or by means of the software thus supplied through the head mounted device 36, are recorded in the database 20, and form the personalized virtual flavors 18 used in FIG. 1.

As an alternative to the arrangements shown in FIGS. 2 and 3, the tanks mounted in a stand-alone manner and delivered through tubes to a cup or other vessel. Such a system is shown in FIG. 4 The basic taste is provided from six tanks 51 containing liquids to provide the basic tastes, namely the sweet, sour, salty, bitter (×2) and umami stimuli, and two additional tanks 52 to provide astringency and a "chilli sensation" (capsaicin). As before, two different solutions are provided for the bitter taste. Smell sensations from separate tanks or capsules 53 can be added The tanks and capsules, 51, 52 and 53 are linked though ducts 54 to a mixer 55. A computer 56 controls valves in the ducts to admit to the mixer a preprogramed amount of each component from the tanks and capsules 51, 52 and 53. The mixer 55 then supplies the programmed mixture to a heater 57 also controlled by the computer 56, and when at the correct temperature the mixture is delivered to a delivery vessel 58, in the illustrated case a beaker. On sampling the content of the beaker, a user can indicate their reaction, for example, too sweet, too strong a smell, insufficient depth of flavor, too hot or cold. The computer is reprogrammed to reflect the user's preference and a further mixture of ingredients delivered to the beaker. This process can be repeated many times until the user is satisfied with the delivered flavor.

The virtual flavor system of the present invention has uses both for individuals, the catering industry, healthcare, gaming, and the food industry. An example would be product selection in which the user selects the real product for which he/she would like to know the flavor, for example by going on line on clicking on the image of the product, a previously determined "experience equivalent" virtual sample is delivered to the user via the virtual flavor system. Another example would be flavor personalization in which a user would choose their preferred multisensory flavor components of a "base product flavor" by changing the taste, smell, colour, etc on the system through a user interface. This choice can be done manually by the user or guided by optimization software. This preference is then matched through QPM1 or QPM2 to a real product blend from the flavor database. Another example is for bending products, say tea, which is being used to illustrate that a personalized choice of virtual flavor can be matched by a blend of rooibos tea product; the flavor of traditional rooibos tea is not to everyone's liking, however the flavor can be altered by blending the natural rooibos with other ingredients, such as rose petals, vanilla, mint, etc. Rooibos tea has been shown to provide a wide range of health benefits, as it is a rich source of dietary antioxidants, including a spalathin, which helps to reduce the output of adrenal gland hormones in the body, reducing stress, regulating blood sugar and lowering the risk of type-2 diabetes and help prevent obesity. Presently, the UK alone throws away £13 bn of food each year, some of this comprises products bought but not liked: this can be reduced by allowing the use of a virtual flavor system according to the present invention prior to purchase.

Although the foregoing examples describe reusable devices in accordance with the invention, a completely disposable device which simply has the virtual flavors in, for example, straws which are tried in a predetermined order, so that the user tastes and/or smells virtual flavors in that order.

One use of the device of the preceding paragraph is to test for potential infections or other medical conditions. For example, loss of smell can be associated a cold or flu, sinusitis, an allergy, and nasal polyps. These issues can also lead to a sensation where a person smells something that is not there, smelling toast and smoke being common, these may cause a reduced sense of smell or a smell of things to come (parosmia).

Loss of both taste and smell is associated with some viral infections and other medical conditions, such as Dementia, including Alzheimer's and Parkinson's disease, and a disposable device of the invention can be used in the diagnosis of a person suspected of having a medical condition. This has come into prominence in recent times because one of the potential markers of COVID-19, is a loss/alteration of taste and smell. The ability as provided by this invention to confirm that has happened, is a useful tool to identify persons who may be so infected, so that they can isolate themselves or be isolated. The loss/alteration of individual tastes and/or smells could be associated with certain medical conditions.

The store 20 may comprise a compressed store of data generated using the techniques described in WO2014/125289 (Warwick University—21 Aug. 2014). Such a store can be used to control the sound and visual effects heard and seen though the head mounted display 30 or any other visual or auditory delivery system, and the taste, mouthfeel, bite and smell sensations to be experienced.

The invention claimed is:

1. A system to deliver to a user artificial flavor sensations equivalent to a selected real flavor comprising:
    a database in which is stored data of a number of real flavors broken down into the individual taste and smell components of each flavor;
    containers containing individual taste components namely: sweetness, sourness, saltiness, bitterness, umami, astringency, capsaicin; each container containing one of said individual taste components;
    a delivery means controlled from the database to provide from the containers a flavor sensation corresponding to the selected real flavor.

2. The system of claim 1 in which the delivery means delivers the taste components of the artificial flavor sensations equivalent to the selected real flavor to a cup or other vessel.

3. The system of claim 1 in which the delivery means delivers the smell components of the artificial flavor sensations equivalent to the selected real flavor to a cup or other vessel.

4. A system to deliver to a user artificial flavor sensations equivalent to a selected real flavor comprising:
- a database in which is stored data of a number of real flavors broken down into the individual taste and smell components of each flavors;
- containers containing individual taste components namely: sweetness, sourness, saltiness, bitterness, umami, astringency, capsaicin; each container containing one of said individual taste components;
- a delivery means controlled from the database delivering the taste and smell components of the selected real flavor to a cup or other vessel.

\* \* \* \* \*